(12) United States Patent
Buxton et al.

(10) Patent No.: US 6,428,808 B1
(45) Date of Patent: Aug. 6, 2002

(54) PHARMACEUTICAL COMPOSITION PREPARED BY ADDITION OF A FLAVOR VEHICLE TO A MEDICAMENT

(75) Inventors: Philip Christopher Buxton, Great Dunmow; Janice Duncan, Worthing; Wendy Johnson, Ealing; Geoffrey David Tovey, Harpenden, all of (GB)

(73) Assignee: SmithKline Beecham p.l.c. (GB)

( * ) Notice: Subject to any disclaimer, the term of this patent is extended or adjusted under 35 U.S.C. 154(b) by 0 days.

(21) Appl. No.: 08/952,426

(22) PCT Filed: May 15, 1996

(86) PCT No.: PCT/EP96/02144

§ 371 (c)(1),
(2), (4) Date: Aug. 21, 2000

(87) PCT Pub. No.: WO96/37188

PCT Pub. Date: Nov. 28, 1996

(30) Foreign Application Priority Data

May 23, 1995 (GB) .............................................. 9510349
Feb. 28, 1996 (GB) .............................................. 9604187

(51) Int. Cl.$^7$ ............................. A61K 9/48; A61K 6/54; A61K 9/20; A61K 9/14
(52) U.S. Cl. ....................... 424/451; 424/452; 424/458; 424/464; 424/489
(58) Field of Search .............................. 424/452, 451, 424/489, 458, 464; 426/590

(56) References Cited

U.S. PATENT DOCUMENTS

| 4,071,614 A | * | 1/1978 | Grimm, III .................. 424/10 |
| 4,520,014 A | * | 5/1985 | Newsome et al. .......... 424/153 |
| 5,560,912 A | * | 10/1996 | Neeman et al. .......... 424/195.1 |
| 5,622,718 A | * | 4/1997 | Al-Shamkhani et al. .... 424/488 |
| 5,716,615 A | * | 2/1998 | Vesely et al. .............. 424/93.4 |
| 5,814,337 A | * | 9/1998 | Merrifield et al. .......... 421/466 |
| 5,817,294 A | * | 10/1998 | Arnold ........................ 424/44 |
| 5,939,447 A | * | 8/1999 | Gorycki et al. ............. 514/382 |
| 6,027,746 A | * | 2/2000 | Lech .......................... 424/455 |
| 6,069,257 A | * | 5/2000 | Giles et al. ................. 548/251 |

FOREIGN PATENT DOCUMENTS

| EP | A 0 022 662 | 1/1981 |
| EP | A 247 980 | 12/1987 |
| EP | A 0 552 105 | 7/1993 |
| WO | 99/04790 | * 2/1999 |

* cited by examiner

Primary Examiner—Thurman K. Page
Assistant Examiner—S. Tran
(74) Attorney, Agent, or Firm—James M. Kanagy; Charles M. Kinzig

(57) ABSTRACT

The invention relates to a method for preparing a flavored liquid medicament, particularly a pediatric preparation in solid form.

2 Claims, 2 Drawing Sheets

PHARMACEUTICAL COMPOSITION PREPARED BY ADDITION OF A FLAVOR VEHICLE TO A MEDICAMENT

This application is a 371 of PCT/EP 96/02144 filed May, 15, 1996.

This invention relates to flavouring systems, particularly for flavouring orally administered pharmaceutical formulations.

Pharmaceutical formulations for oral administration are often provided in a made up liquid form ready for dispensing by a chemist or pharmacist and consumption by the patient without dilution. Alternatively such formulations are provided in a concentrated liquid form for reconstitution with a convenient volume of water or other palatable aqueous medium just prior to ingestion. Further alternative formulations may be in the form of a dry powder or granules suitable for reconstitution. Many examples of such formulations are known in the art. The active constituents of such formulations and/or the excipients sometimes have an unpleasant taste, and therefore a flavouring material is usually included in such formulations. This is particularly the case with paediatric formulations.

A problem arises in that preferences for the taste of such flavourings often varies between patients or groups of patients, such as patients of different nationalities with local taste preferences. For example a flavour which may be acceptable or preferred in one country may be less acceptable in another country, or one flavour may be unacceptable to individual paediatric patients whilst a different flavour may be preferred. Also the problem of "flavour fatigue" may be experienced, in that a patient may become tired of repeated doses of the same, albeit pleasant, flavoured medicament Normally pharmaceutical formulations are made up as a bulk including the flavouring material. Consequently any need to prepare alternative flavoured formulations requires preparation of separate bulk quantities of flavoured formulation, and the possibility of suiting differing individual preferences for flavours is limited. In addition, flavours are normally provided in the form of intensely flavoured materials which cannot be conveniently handled by individual patients in the small quantities in which they are present in an individual supply or dose.

It is therefore desirable to provide a method by means of which unit or individual dosages or other small quantities of oral formulations can be easily and individually flavoured. In particular in the case of paediatric formulations it is also desirable to provide any flavouring system in an attractive and appealing form.

In a first aspect the present invention provides a method for preparing a flavoured liquid medicament which comprises addition of a flavouring vehicle to a medicament.

By the term "flavouring vehicle" is meant any suitable flavouring means capable of releasing flavouring into a liquid medicament, including dosage means such a tablet or a capsule containing an aliquot of powder or liquid containing a pharmaceutically acceptable flavouring substance. Alternatively, the flavouring vehicle can be a flavouring substance per se, either in neat form, or preferably in the presence of a pharmaceutically acceptable carrier or excipient. Preferably the flavouring vehicle is an aliquot of powder or liquid containing a pharmaceutically acceptable flavouring substance which is added to the unflavoured medicament, said flavouring being initially contained in a capsule or sachet.

Other flavouring vehicles within the scope of the invention include a flavour impregnated package, for example a bottle having a lid impregnated with flavouring. The bottle is of a suitable size for a course of treatment and the patient can select from lids having alternative impregnated flavours. Further alternatives are oral syringes or dosing cups impregnated with flavouring.

A further flavouring vehicle within the scope of the invention comprises an edible solid substrate in the form of a wafer or thin sheet of a water-dispersible or water-soluble non-toxic material which dissolves and/or disperses in an aqueous media. The wafer has a sufficient quantity of an edible flavouring substance impregnated in or deposited on its surface, such that the flavouring substance passes into the aqueous medium on dissolution or dispersion of the substrate therein and imparts a palatable flavour to the liquid material.

Preferably the flavouring vehicle is a capsule or sachet each of which contains an aliquot of liquid or powdered flavouring. Other preferred flavouring vehicles are tablets or flavoured wafers. More preferably the flavouring vehicle is a sachet or a capsule. Most preferably the flavouring vehicle is a sachet or a capsule containing a liquid flavouring formulation which is the added to the liquid medicament, i.e. the contents of the capsule or sachet are added.

By the term "capsule" is meant any receptacle capable of containing a flavouring. The flavouring within the capsule can be an aliquot of liquid or powder, preferably the capsule will contain the flavouring in liquid form. Such capsules can be manufactured from any suitable synthetic or natural material, for example polyethylene or gelatin. In the case of capsules which are to be added to the medicament, the capsule shell is preferably made of a substance which is readily soluble in water or aqueous media, for example starch. Alternative capsules, which are preferred, are those which can contain an aliquot of powder or liquid and can be opened by the patient or pharmacist and the contents then added to the formulation. Such capsules include those having a frangible portion, for example ampoules and the like. The advantage of this type of capsule is that there is no time delay while the capsule shell dissolves.

By the term "sachet" is meant any packet capable of containing a flavouring. The sachet can be made of any suitable material including paper, plastic or foil so that it can be opened by the patient or pharmacist and the contents then added to the formulation.

By the term "liquid medicament" is meant a formulation comprising a drug substance in liquid form, for example a solution, suspension, emulsion or syrup. The liquid medicament can be any pharmaceutical formulation which is in solution, suspension, emulsion or syrup form, including formulations which have been made up as described above by reconstitution of a concentrate. The flavouring substance dissolves or disperses in the formulation to impart it's flavour thereto. In a further aspect of the invention the dosage means can be added to a dry or liquid form of medicament prior to reconstitution or dilution.

Preferably the tablet, powder or liquid flavouring material will be of a type which dissolves or disperses rapidly in contact with the liquid medicament, typically within a few seconds, or at most a few minutes, so that the flavour passes rapidly into the liquid material.

The quantity of flavouring substance may be such that when the flavouring substance passes into the pharmaceutical formulation which includes an active ingredient and/or excipients which have a strong, unpleasant or otherwise unacceptable taste, the taste is masked to such an extent that the taste of the liquid material becomes palatable. Preferably the quantity of flavouring substance should be sufficient such that addition of one or more of the dosage means imparts an acceptable flavour to a volume of made up liquid which is normally dispensed by the pharmacist sufficient for a course of treatment of a patient, for example ca 50–600 ml, or consumed as a unit dose by the patient. The quantity of flavouring substance may need to be increased, and/or more of the substrates used if the system is intended for use with a formulation in which the active constituents and/or excipients therein have a particularly strong taste.

The flavouring substance may be any edible flavouring substance which is acceptable and approved for use with foods and/or pharmaceutical formulations. Very many such substances are known. The flavouring substance may for example be a natural or artificial flavouring, such as of a fruit, vegetable or confectionery taste. If desired more than one flavouring can be used in a single dosage means. Additionally or alternatively the flavouring substance may comprise a sweetener, such as sugar, sodium saccharin or aspartame.

The dosage means of the invention can contain the flavouring substance in neat form or the flavouring substance can itself be mixed with a suitable pharmaceutically acceptable carrier or excipient. In the case of a capsule or sachet, the flavouring substance can be present as a solid or a solution, for example as an aqueous solution.

In addition to the flavouring substance, the dosage means may have therein or deposited on its surface a colouring substance which is acceptable and approved for use with foods and pharmaceutical formulations. Very many such substances are known. The colouring substance may be a natural or artificial colouring, and may be selected on the basis of being appropriate to the flavouring substance, e.g. yellow for a banana flavouring, or on the basis of a colour associated with the supplier, e.g. a corporate symbol, or associated with a pharmaceutical formulation with which it is intended for use. The flavouring substance may itself be suitably coloured, or alternatively the colouring substance may have a suitable flavour, so that a single substance may fulfill both flavour and colour functions.

The flavouring means and method of the invention are suitable for use to impart flavour to pharmaceutical formulations which require or benefit from flavouring to make them more palatable. Such formulations may be of any type, e.g. antibiotic, anti-asthma, anti-tussive, analgesic, anti-inflammatory, anti-depressant etc. Particularly suitable formulations are those routinely administered to paediatric patients, in particular antibiotic, anti-asthma, anti-tussive and analgesic formulations. Particularly preferred are formulations containing the anti-asthma compound 4-oxo-8-[4-(4-phenylbutoxy)benzoylamino]-2-(tetrazol-5-yl)-4H-1-benzopyran or a pharmaceutically acceptable salt thereof, that is to say the compound having the INN Pranlukast. Other preferred formulations are those containing antibiotics such as amoxycillin.

Typically in use, bulk unflavoured pharmaceutical formulations can be prepared at a central source, and packaged in individual containers each of which contains a supply sufficient for a course of treatment of a patient, that is to say one or more unit doses. Each such package may be supplied with one or more of the above-described dosage means in one or more flavours which suits the patient's preference. Either the pharmacist or the patient can add one or more dosage means of the invention to achieve an acceptable flavour. In the case where patients are personally adding the dosage means, capsules, tablets, sachets or wafers are generally preferred as they are easier and safer to handle.

The liquid formulation may be a formulation prepared by the reconstitution by the user of a dry powder, granules or a water-dispersible or soluble tablet with water or an aqueous medium. The flavouring system may be introduced into the formulation after reconstitution, e.g. into a made up unit dose in a drinking vessel. Alternatively the flavouring system may be added to the powder or granules prior to reconstitution before water or aqueous medium is added, e.g. to a bulk container of the powder or granules containing several unit doses of the formulation. Alternatively the flavouring system may be introduced to the formulation at the same time as the water or aqueous medium. In this latter mode the bulk can be reconstituted and the flavouring system will then impart its flavour to the made up bulk liquid.

In another aspect the invention provides a kit comprising a course of liquid medicament, or a concentrate therefor, together with one or more dosage means containing flavouring.

In a further aspect the invention provides a pharmaceutical composition prepared by addition of a dosage means containing flavouring to a medicament.

The problem of flavouring liquids which are to be drunk is not confined to pharmaceutical formulations. Many drinks, e.g. milk based drinks, can be flavoured by the addition of solid flavourings, e.g. compacted tablets or powders or granulates in sachets or other containers, or capsules. For example GB 1176087 discloses effervescent sweetener tablets, EP 0124663 discloses compacted sweetening and flavouring tablets, EP 0082459 and EP 0082460 disclose flavourant capsules. These known products result in the problem of relative inconvenience and there is a need for a more convenient alternative, and/or an alternative that provides other novel benefits.

According to a further aspect of the invention, a flavouring system, for flavouring a drinkable liquid material, comprises an edible solid substrate in the form of a wafer or thin sheet of a water-dispersible or water-soluble non-toxic material which dissolves and/or disperses in an aqueous media to produce a drinkable solution or suspension, the substrate having a sufficient quantity of an edible flavouring substance impregnated in or deposited on its surface such that the flavouring substance passes into the aqueous medium on dissolution or dispersion of the substrate therein and imparts a palatable flavour to the liquid material.

The drinkable liquid may be an oral pharmaceutical formulation as described above or preferably a drink such as milk-based drink.

The edible solid substrate is preferably pharmaceutically acceptable and should be made of a material which dissolves or disperses rapidly in contact with the liquid material. Such a time is generally suitable if the flavouring system is used to impart flavour to a liquid pharmaceutical formulation shortly after it is made up from a concentrate, or to a drink for short-term consumption. Suitable materials for such a substrate are known, for example compacted fibrous or particulate edible materials such as carbohydrates, for example polysaccharides such as starch and cellulose based materials. An example of such a material is rice paper, which readily disintegrates and disperses in water or other aqueous media, to form a palatable dispersion.

Suitably the flavouring system of the invention may be made by the process of applying the flavouring substance to a pre-made up substrate, e.g. a solid absorbent substrate.

The substrate may suitably be in the form of a small wafer, typically 0.5–2 mm in thickness, and typically 1–5 cm in width. Wafers may be provided individually or separably linked together for example in the form of a strip or sheet of individual wafers linked together by weak links, for example the wafer being delineated by thinned or perforated lines across an otherwise continuous strip or sheet. In such a strip of sheet individual wafers may all have the same flavouring substance or individual wafers may differ in the nature of their flavouring substance. Wafers may be in any particular shape to suit the preferences of individual patients or markets. For example wafers may be simple geometric shapes such as squares rectangles, circles, triangles, hexagons etc.

Alternatively the wafers may be made in shapes which are suggestive of the flavouring substance, e.g. in a shape representing a fruit etc. Alternatively the wafers may be made in a shape related to a trade mark or other symbol associated with the supplier. Alternatively, particularly for paediatric patients the wafer may be made in a shape which is appealing to children, such as a novelty character etc. The substrate may additionally be embossed in some appropriate way, for example for decoration, to provide an embossed symbol such as a symbol associated with the supplier or a pharmaceutical formulation with which it is to be used, or with Braille text to assist the partly sighted.

The flavouring substance may be impregnated in or deposited on its surface by known techniques. For example the flavouring substance may be mixed with the fibres or particles before these are compacted, or alternatively the substrate may be made first then the flavouring substance may be impregnated into it or deposited thereon, for example as a liquid, which may be the neat flavouring substance itself, or a solution or solvent thereof, e.g. in a volatile solvent which may be water. Suitable techniques for doing this will be apparent to those skilled in the art.

The quantity of flavouring substance impregnated in or deposited onto the substrate will depend upon the nature of the flavouring substance and the application to which the flavouring system is to be put Suitably the quantity of flavouring substance should be sufficient so that addition of one or more of the substrates imparts an acceptable flavour to a suitable volume of made up liquid.

Additionally or alternatively the substrate may have printed thereon a symbol, for example a symbol representing the flavouring substance, such as a representation of a fruit etc. Such a symbol may additionally or alternatively be associated with the supplier, for example a trade mark, or with a pharmaceutical formulation with which it is intended for use. Additionally or alternatively the substrate may have printed thereon text conveying information to the user. If such matter is printed onto the substrate, then the ink used should be an ink substance which is acceptable and approved for use with foods and pharmaceutical formulations. The ink may itself contain all or at least part of the flavouring substance, so that the flavouring substance and such a symbol may be deposited onto the substrate in a single operation.

In one form of the invention, suitable for flavouring milk-based drinks which at least initially have a frothy surface, the colouring may be such that if the wafer is deposited on the upper surface of the froth, the dissolution or dispersion of the wafer bearing a coloured symbol as described above may leave a coloured after image in the shape of the symbol on the froth. This can have an attractive effect.

Therefore as an alternative aspect of this invention there is provided a method of imparting a flavour to a drinkable liquid pharmaceutical formulation, which comprises the step of introducing into the liquid formulation a flavouring system comprising an edible solid substrate which dissolves and/or disperses in an aqueous medium to produce a drinkable solution or suspension, the substrate having a sufficient quantity of an edible flavouring substance impregnated in or deposited on its surface such that the flavouring substance passes into the aqueous medium on dissolution or dispersion of the substrate therein and imparts a palatable flavour to the formulation.

The invention also provides a method of imparting a flavour to a drinkable liquid material by the introduction of a flavouring substance into the liquid material by means of a flavouring system as described above.

The invention also provides the use of a flavouring system as described above for the importation of a flavour to a drinkable liquid material.

The invention also provides a flavouring system as described above provided for the purpose of imparting a flavour to a drinkable liquid material.

The invention also provides one or more flavouring systems as described above provided in combination with one or more unit doses of an oral pharmaceutical formulation or of a concentrate for reconstitution with an aqueous medium into an oral pharmaceutical formulation.

The invention will now be described by way of example only with reference to the accompanying figures which are representative of the invention only and not intended to limit the generality of this disclosure.

Figure 1:
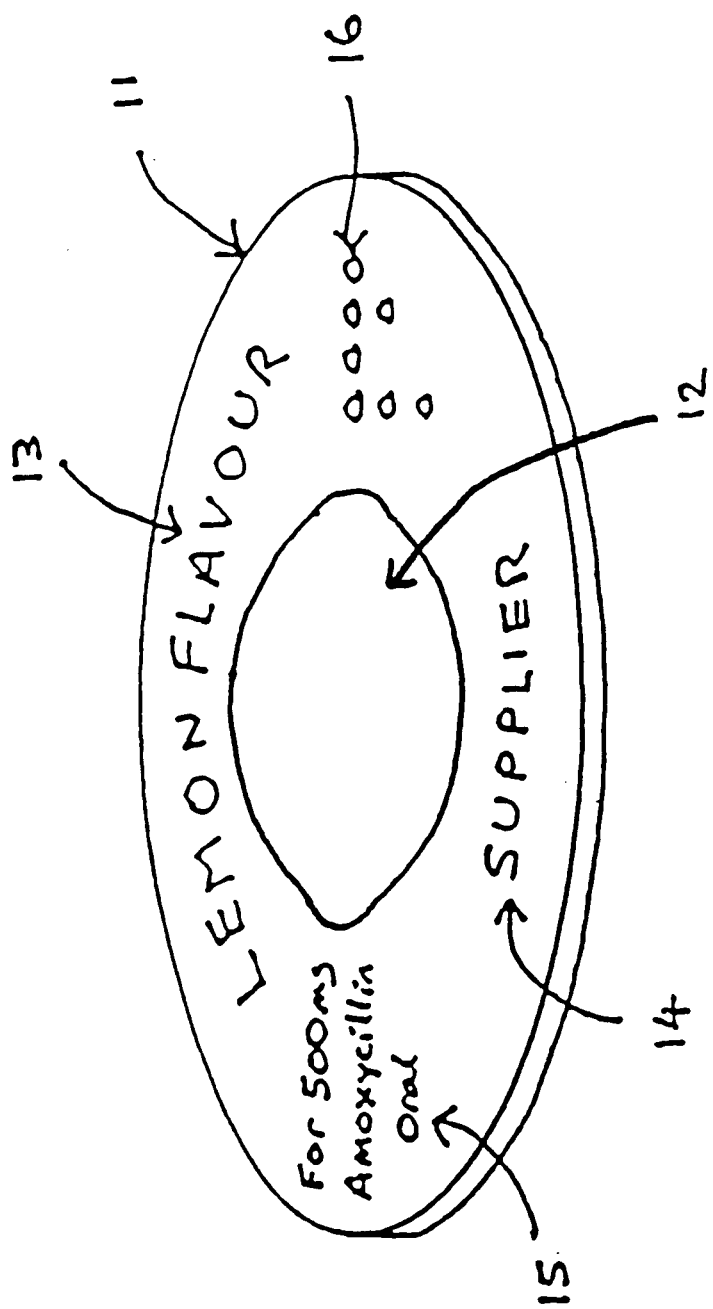
FIG. 1 shows a perspective view of a flavouring system of the invention in the form of a circular wafer.

Referring to FIG. 1, a flavouring system comprises a circular wafer (11) of rice paper, about 1 mm thick and about 3 cm in diameter. The wafer (11) is impregnated with a lemon/lime flavouring substance corresponding to about 28 mg of lemon dry flavour and 1.4 mg of lime dry flavour. The wafer (11) is imprinted with a symbol of a lemon (12) in yellow colouring, and with wording (13), (14), (15) stating respectively the flavour, the supplier and its intended use, i.e. as a flavouring system for a 500 mg oral amoxycillin suspension. The wafer (11) is also embossed with Braille lettering (16) indicating the nature of the wafer. Although all of the printing (12–15) and embossing (16) is shown in FIG. 1 as being located on one face of the wafer (11), some of it could be located on the opposite face, and some of the printing and/or embossing shown could of course be omitted.

Figure 2:
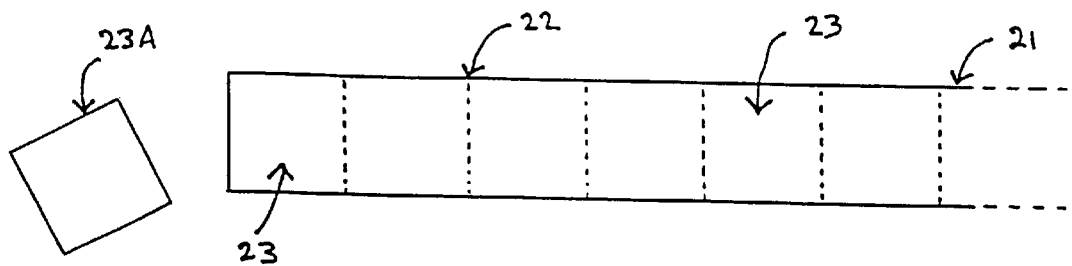
FIG. 2 shows a view of a flavouring system of the invention in the form of a strip of rectangular wafers.

Referring to FIG. 2, a flavouring system comprises a strip (21) of rice paper, about 1 mm thick, divided up by perforated lines (22) across the strip (21) into individual rectangular wafers (23), each of which is about 2.5 cm square. The entire strip is impregnated with a lemon/lime flavouring substance, so that each wafer of FIG. 2 contains sufficient of the flavouring substance to impart a desired intensity of flavour to a unit oral dose of a pharmaceutical formulation when in a volume of water appropriate for drinking. Each wafer (23) also bears a symbol, wording and embossing (not shown) as on the wafer of FIG. 1. Wafers (23A) may easily be broken off the strip (21) at the perforated lines (22).

Figure 3:
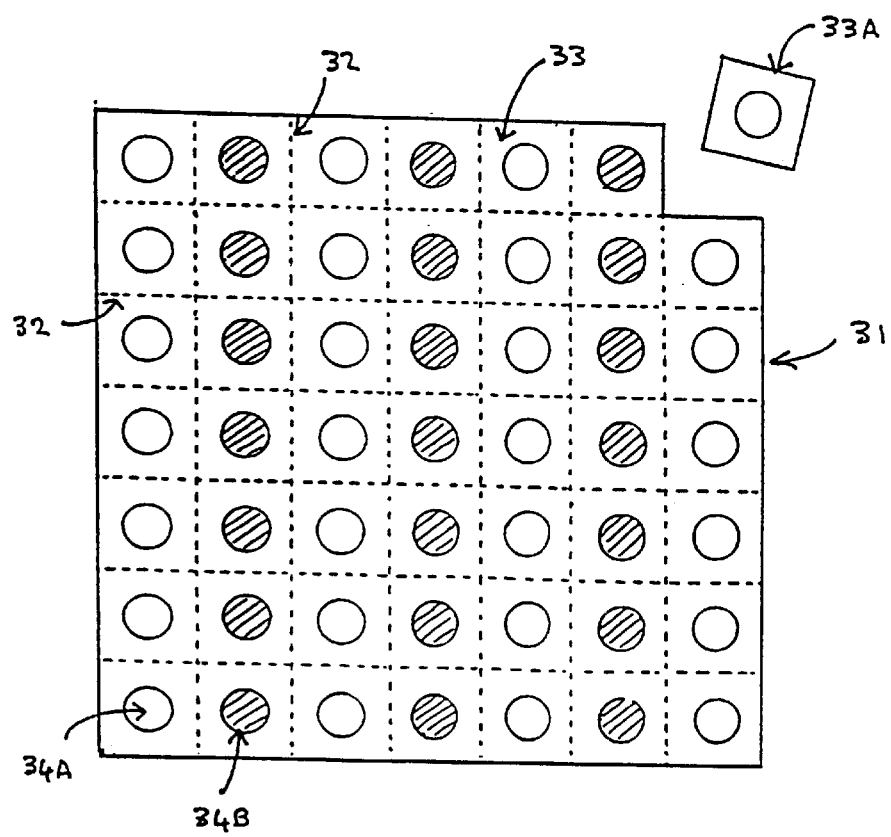
FIG. 3 shows a view of a flavouring system of the invention in the form of a sheet of rectangular wafers.

Referring to FIG. 3, a flavouring system comprises a sheet (31) of rice paper, divided up by a grid pattern of perforated lines (32) which delineate individual rectangular wafers (33). The sheet (31) is about 1 mm thick, and individual wafers (33) are each about 2.5 cm square.

Each wafer (33) has imprinted thereon a symbol (34A, 34B), in a coloured ink which also includes a flavouring substance. Alternative rows of the wafers (33) are imprinted with symbols (34A, 34B) which include a different flavouring substance, and the symbol (34A, 34B) is selected so as to be appropriate to the flavouring substance, for example a symbol of an orange indicating an orange flavouring substance. Each wafer (33) may also bear wording and embossing (not shown) as shown in FIG. 1. Wafers (33A) may easily be broken off the sheet at the perforated lines (32).

In use, to a pharmaceutical formulation in liquid form, for example made by reconstituting a dry tablet or granular formulation from a sachet in ca. 100 ml water, for oral administration is added one or more of the individual wafers (11, 23A, 33A), either all of the same flavour or of different flavours to suit individual taste preference. The wafer (11, 23A, 33A) disintegrates in the liquid formulation, and its dissolution and/or dispersion may be encouraged by agitation or stirring of the liquid. Upon disintegration of the wafer (11, 23A, 33A) the flavouring substance is dispersed or dissolved in the formulation, thereby imparting its taste to the formulation.

Example 1

A reconstitutable formulation containing 250 mg of the antibiotic amoxycillin can be made palatable by the use of 28 mg of lemon dry flavour plus 1.4 mg of lime dry flavour plus 2.5 mg of sodium saccharin. These quantities of flavouring substance can easily be impregnated into or deposited on the surface of a wafer as described herein.

Example 2

A water soluble flavouring granule, for example a carbohydrate or sugar based granule, can be sprayed with one or more flavouring components, for example orange flavour 1, 2 or 3 or mixtures thereof. A sweetner and colouring agent can be added if required. Suitable quantities of the resulting mixture can be filled into sachets or capsules using standard filling equipment.

What is claimed is:

1. A method for preparing a flavoured liquid medicament which comprises addition of a flavouring vehicle to a medicament in which the medicament is 4-oxo-8-[-4-(4-phenylbutoxy)benzoylamino]-2-(tetraxol-5-yl)-4H-1-benzopyran or a pharmaceutically acceptable salt thereof and a pharmaceutically acceptable excipient.

2. A pharmaceutical composition prepared by addition of a flavour vehicle containing flavouring to a medicament in which the medicament is 4-oxo-8-[4-(4-phenylbutoxy)benzoylamino]-2-(tetraxol-5-yl)4H-1-benzopyran or a pharmaceutically acceptable salt thereof.

\* \* \* \* \*